United States Patent [19]

Jung et al.

[11] Patent Number: 5,380,735
[45] Date of Patent: Jan. 10, 1995

[54] BENZOTHIAZOLE DERIVATIVES AND METHODS OF USE

[75] Inventors: Bon Y. Jung, Daejeon; Choon S. Ra, Seoul; Yo S. Rew; Young H. Rhee, both of Daejeon; Ho S. Yeo; Man Y. Yoon, both of Daejeon; Woo B. Choi, Daejeon, all of Rep. of Korea

[73] Assignee: Lucky, Ltd., Seoul, Rep. of Korea

[21] Appl. No.: 126,658

[22] Filed: Sep. 27, 1993

[30] Foreign Application Priority Data

Sep. 28, 1992 [KR] Rep. of Korea .................. 92-17670

[51] Int. Cl.$^6$ .................. A61K 31/425; C07D 277/70; C07D 277/82; C07D 277/68
[52] U.S. Cl. .................................... 514/367; 548/161; 548/164; 548/170
[58] Field of Search ................ 514/367; 548/161, 164, 548/170

[56] References Cited

U.S. PATENT DOCUMENTS 4,999,042 3/1991 Anthony et al. .................... 514/367
5,003,073 3/1991 Ascher ................. 548/170

FOREIGN PATENT DOCUMENTS 0299694 1/1989 European Pat. Off. .

OTHER PUBLICATIONS

The Journal of Antibiotics, "The Strobilurins-New Antifungal Antibiotics From The Basidiomycete *Strobilurus Tenacellus*," T. Anke et al., Oct. 1977, vol. 30, pp. 806–810.
Organic Syntheses Collective, C. F. H. Allen et al., vol. 3, 1955, pp. 76–78.
Organic Syntheses Collective, Robert L. Frank et al., vol. 3, 1955, pp. 735–736.

*Primary Examiner*—Joseph Paul Brust
*Assistant Examiner*—Mary Susan H. Gabilan
*Attorney, Agent, or Firm*—Willian Brinks Hofer Gilson & Lione

[57] ABSTRACT

The present invention relates to a novel benzothiazole derivative of the following general formula (I) or its (E), (Z)isomer, and processes for preparation thereof,

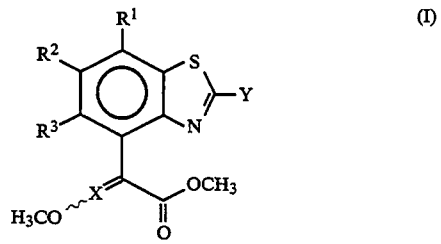

in which $R^1$, $R^2$ and $R^3$ independently of one another represent hydrogen, halogen, straight and branched ($C_1$-$C_8$)alkyl, ($C_1$-$C_8$)halogenoalkyl or ($C_1$-$C_8$)alkoxy, X represents N or CH, Y represents a group -$OR^4$, $SR^5$ or

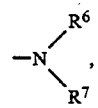

$R^4$, $R^5$, $R^6$ and $R^7$ independently of one another represent hydrogen, straight and branched ($C_1$-$C_{16}$)alkyl, ($C_3$-$C_8$)alkenyl, ($C_3$-$C_8$)alkynyl, ($C_3$-$C_8$)cycloalkyl, alkyl substituted with ($C_1$-$C_6$)alkoxy or ($C_1$-$C_6$)halogenoalkyl, or represent a substituted phenyl, phenylacyl or benzyl group wherein the possible substituent on the phenyl, phenylacyl or benzyl group includes halogen, straight and branched ($C_1$-$C_8$)alkyl, ($C_1$-$C_8$)alkoxy, ($C_3$-$C_8$)alkenyl, ($C_3$-$C_8$)alkynyl, phenoxy, nitro, cyano and a five- or six-membered heterocyclic group containing one to four nitrogen atoms.

The compound of formula (I) is useful for combating phythopathogenic organisms and fungi present on animal.

5 Claims, No Drawings

BENZOTHIAZOLE DERIVATIVES AND METHODS OF USE

BACKGROUND OF THE INVENTION

1. Field of the Invention

The present invention relates to a novel benzothiazole derivative having the following general formula (I),

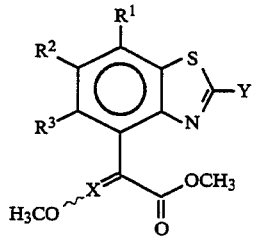

in which

R¹, R² and R³ independently of one another represent hydrogen, halogen, straight and branched ($C_1$-$C_8$)alkyl, ($C_1$-$C_8$) halogenoalkyl or ($C_1$-$C_8$)alkoxy, X represents N or CH, Y represents a group -OR⁴, -SR⁵ or

and

R⁴, R⁵, R⁶ and R⁷ independently of one another represent hydrogen, straight and branched ($C_1$-$C_{16}$)alkyl, ($C_3$-$C_8$) alkenyl, ($C_3$-$C_8$)alkynyl, ($C_3$-$C_8$)cycloalkyl, alkyl substituted with $C_1$-$C_6$)alkoxy or ($C_1$-$C_6$)halogenoalkyl, or represent a substituted phenyl, phenylacyl or benzyl group wherein the possible substituent on the phenyl, phenylacyl or benzyl group includes halogen, straight and branched ($C_1$-$C_8$)alkyl, ($C_1$-$C_8$)alkoxy, ($C_3$-$C_8$)alkenyl, ($C_3$-$C_8$)alkynyl, phenoxy, nitro, cyano and a five- or six-membered heterocyclic group containing one to four nitrogen atoms.

The present invention also relates to a process for preparation of the benzothiazole derivative of formula(I), as defined above, and the use of the benzothiazole derivative(I) for combating phythopathogenic organisms and fungi present on animal.

2. Background Art

In 1977, Anke et. al. (J. of Antibiotics 30, 806 (1977)) have reported strobillurin A having a potent and broadspectrum microbicidal activity:

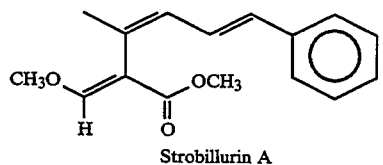

Strobillurin A

Thereafter, many studies for providing numerous compounds analogous to strobillurin A have been made.

In 1987, European Laid-open Patent Publication No. 299694 (Cliff, et. al.) has disclosed the compound of formula (III) having a potent microbicidal activity against various fungi, particularly against apple scab causative organism (*Venturia inaequalis*), grape downy mildew causative organism (*Plasmopara viticola*) etc.

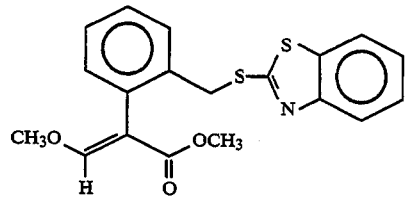

In addition, numerous analogous compounds including the compound of formula (IV) disclosed in German Laid-open Patent Publication No. 3,939,258 (Klausener, 1989) and the compound of formula (V) disclosed in European Laid-open Patent Publication No. 480,798 (Benoit), both of which are bicyclic compounds similar to the compound (I) according to the present invention and have been reported as having a potent microbicidal activity, have been developed.

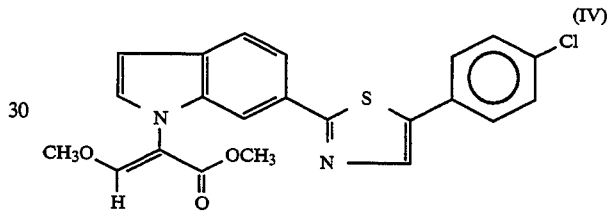

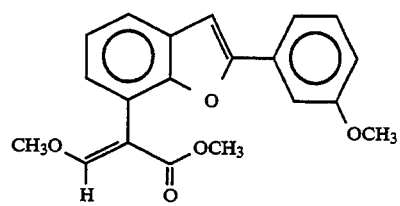

On the basis of the above mentioned prior art, the present inventors have prepared numerous strobillurin A analogous compounds and studied their microbicidal activities. As a result, we have found that a certain compound having a benzothiazole derivative as the lipophilic group exhibits potent broad-spectrum microbicidal activity against phythopathogenic organisms and fungi present on animal.

Therefore, it is an object of the present invention to provide a novel benzothiazole derivative of formula(I), as defined above, which has a potent broad-spectrum microbicidal activity.

It is a further object of this invention to provide a process for preparing the novel benzothiazole derivative of formula(I).

It is a further object of this invention to provide a use of the novel benzothiazole derivative of formula(I) for combating phythopathogenic organisms and fungi present on animal.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to a novel benzothiazole derivative having the following general formula (I),

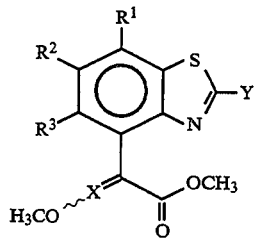

in which
$R^1$, $R^2$ and $R^3$ independently of one another represent hydrogen, halogen, straight and branched $(C_1-C_8)$alkyl, $(C_1-C_8)$ halogenoalkyl or $(C_1-C_8)$alkoxy,
X represents N or CH,
Y represents a group $-OR^4$, $-SR^5$ or

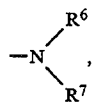

and
$R^4$, $R^5$, $R^6$ and $R^7$ independently of one another represent hydrogen, straight and branched $(C_1-C_{16})$alkyl, $(C_3-C_8)$ alkenyl, $(C_3-C_8)$alkynyl, $(C_3-C_8)$cycloalkyl, alkyl substituted with $(C_1-C_6)$alkoxy or $(C_1-C_6)$halogenoalkyl, or represent a substituted phenyl, phenylacyl or benzyl group wherein the possible substituent on the phenyl, phenylacyl or benzyl group includes halogen, straight and branched $(C_1-C_8)$alkyl, $(C_1-C_8)$alkoxy, $(C_3-C_8)$alkenyl, $(C_3-C_8)$alkynyl, phenoxy, nitro, cyano and a five- or six-membered heterocyclic group containing one to four nitrogen atoms.

Since the compound of formula (I) contains one carbon-carbon or carbon-nitrogen double bond in its structure, the compound of formula (I) can exist in the form of two separable geometric isomers, i.e. (E)-isomer and (Z)-isomer. The present invention also includes (E)-isomer and (Z)-isomer of the compound of formula (I).

The compound of formula (I) according to the present invention is active against various pathogenic organisms, particularly against phythopathogenic organism and fungi present on animal. Such pathogenic organisms include *Erysiphe graminis* causative of powdery mildew, *Plasmopara viticola* causative of grape downy mildew, *Pyricularia oryzae* causative of rice blst, *Rhizoctonia solani* causative of rice sheath blight, *Botrytis cinerea* causative of gray mold, *Puccinia recondita* causative of wheat rust, *Venturia inaequalis* causative of apple scab, etc., and further pathogenic organisms causative of other powdery mildew and rust, and also other pathogens such as Deuteromycetes, Ascomycetes, Phycomycetes and Basidiomycetes.

Preferably, in the compound of formula(I) $R^1$, $R^2$ and $R^3$ independently of one another represent hydrogen, fluoro, chloro, methyl or ethyl and $R^4$, $R^5$, $R^6$ and $R^7$ independently of one another represent hydrogen, straight and branched$(C_1-C_6)$alkyl, $(C_3-C_6)$alkenyl or $(C_3-C_6)$alkynyl. More preferably, in the compound of formula(I) $R^4$, $R^5$, $R^6$ and $R^7$ independently of one another represent a phenyl group substituted with straight and branched $(C_1-C_6)$alkyl, $(C_3-C_6)$alkenyl, $(C_1-C_6)$alkoxy, $(C_3-C_6)$alkynyl, phenoxy, halogen, pyridinyl, pyrimidinyl, thiazolyl or imidazolyl on 2-, 3- or 4-position.

In another aspect of the present invention, it has been also found that the compound of formula (I) wherein Y is

said compound being represented by formula (I'), can be prepared by the process characterized in that:

(a) a compound of formula (VI) is substituted with a halogen and then reacted with an alkyl or acyl halide under basic condition to obtain a compound of formula (VII), (b) the compound of formula (VII) is subjected to a halogen-lithium substitution reaction and then reacted with dimethyloxalate to obtain a compound of formula (VIII), and (c) the compound of formula (VIII) thus obtained is reacted with methoxylamine under basic condition or subjected to a Wittig reaction with a phosphorus ylide,

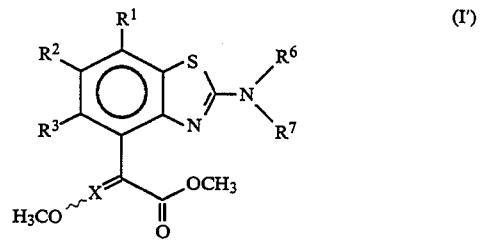

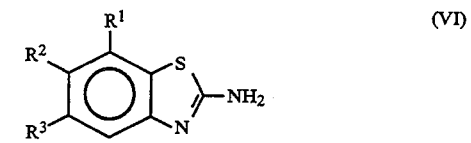

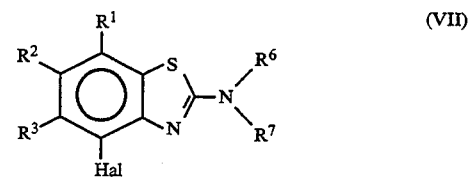

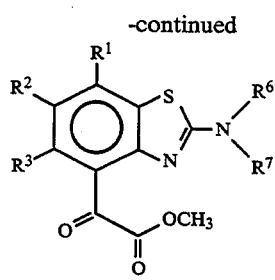

(VIII)

in which

R[1], R[2] and R[3] independently of one another represent hydrogen, halogen, straight and branched ($C_1$-$C_8$)alkyl, ($C_1$-$C_8$)halogenoalkyl or ($C_1$-$C_8$)alkoxy, X represents N or CH, R[6] and R[7] independently of one another represent hydrogen, straight and branched ($C_1$-$C_{16}$)alkyl, ($C_3$-$C_8$)alkenyl, ($C_3$-$C_8$)alkylnyl, ($C_3$-$C_8$)cycloalkyl, alkyl substituted with ($C_1$-$C_6$)alkoxy or ($C_1$-$C_6$)halogenoalkyl, or represent a substituted phenyl, phenylacyl or benzyl group wherein the possible substituent on the phenyl, phenylacyl and benzyl group includes halogen, straight and branched ($C_1$-$C_8$)alkyl, ($C_1$-$C_8$)alkoxy, ($C_3$-$C_8$)alkenyl, ($C_3$-$C_8$)alkynyl, phenoxy, nitro, cyano and a five- or six-membered heterocyclic group containing one to four nitrogen atoms, and Hal represents a halogen atom.

The compound of formula (VI) which is required as a starting material in the above process can be synthesized according to the following two different methods which have been described in literature, Organic Synthesis, Coll. Vol. 3, 76(1955) and Organic Synthesis, Coll. Vol. 3, 734 (1955). Specifically, the benzothiazole derivative of formula(VI) can be prepared by reacting a substituted aniline with ammonium thiocyanate to prepare a thiourea which is then cyclized. Alternatively, the compound of formula (VI) can also be prepared by reacting aniline with benzoyl thiocyanate to obtain benzoyl thiourea, and then removing a benzoyl group with a base (see Organic Synthesis, Coll. Vol. 3, 734(1955)).

The compound of formula (VII) can be prepared starting from the compound of formula (VI), for example, by introducing a bromo substituent into 4-position of benzothiazole group and then reacting an amino group present in 2-position with an alkyl halide or an acyl halide under basic condition. This reaction is based on a specific substitution property of the compound of formula(VI), that is, when R[2] in the compound of formula (VI) is not hydrogen but alkyl (e.g. methyl, ethyl, etc.) or halogen (e.g. fluoro, chloro, etc.), then only the 4-position of benzothiazole nucleus can be halogenated.

The compound of formula (VIII) can be synthesized from the compound of formula (VII) by replacing halogen with lithium according to a halogen-lithium substitution reaction and subsequently reacting with dimethyloxalate. Suitable lithium compound which can be used in this reaction is n-butyl lithium, sec-butyl lithium, tert-butyl lithium, etc; and a suitable solvent which can be used is an ether such as tetrahydrofuran, diethylether, dimethoxyethane and the like.

The desired compound of formula (I') wherein X is N can be synthesized by reacting the compound of formula (VIII) with methoxylamine under basic condition and, alternatively, the compound of formula (I') wherein X is CH is prepared by means of a Wittig reaction with phosphours ylide.

In this reaction, a suitable base is an organic base such as triethylamine, pyridine and the like, and an inorganic base such as sodium hydrogen carbonate, sodium carbonate, potassium carbonate and the like; and a suitable solvent is a ketone such as acetone, methylethylketone and the like, an ether such as tetrahydrofuran, diethylether and the like, a halogenated hydrocarbon such as dichloromethane, dichloroethane, chloroform and the like, and alcohol such as methanol, ethanol and the like etc., with an alcohol being most preferably used. The reaction temperature is 0° C. to 120° C. and most preferably 20° C. to 80° C.

In the Wittig reaction with phosphonium salt, for example, methoxymethyltriphenyl phosphonium chloride can be used as the phosphonium salt; a base which can be used is butyl lithium, potassium t-butoxide, sodium ethoxide, sodium methoxide, dimsyl (dimethylsulfoxide) anion and the like; and a suitable solvent which can be used is an ether such as tetrahydrofuran, diethyl ether and the like.

Further, according to the present invention the compound of formula (I) wherein Y is -OR[4], said compound being represented by formula (I''), can be prepared by the process characterized in that:

(a) a compound of formula (VI') is diazotized with sodium nitrite and then substituted with a halogen to obtain a compound of formula (IX), (b) the compound of formula (IX) is reacted with an alcohol under basic condition to obtain a compound of formula (X), and (c) the compound of formula (X) is subjected to a halogen-lithuim substitution reaction and then reacted with dimethyloxalate to obtain a keto ester which is then reacted with methoxylamine under basic condition or subjected to a Wittig reaction with phosphorus ylide,

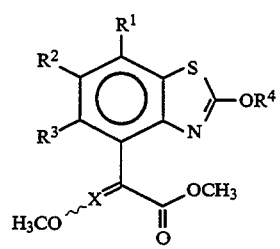

(I'')

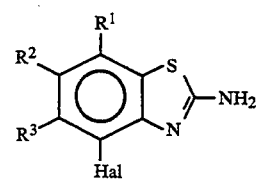

(VI')

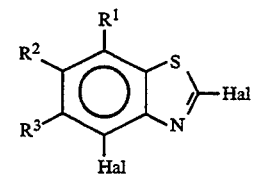

(IX)

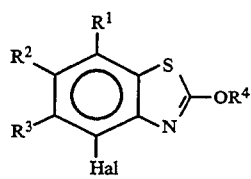

(X)

in which

R¹, R² and R³ independently of one another represent hydrogen, halogen, straight or branched ($C_1$-$C_8$)alkyl, ($C_1$-$C_8$)halogenoalkyl or ($C_1$-$C_8$)alkoxy, X represents N or CH, R⁴ represents hydrogen, straight and branched ($C_1$-$C_{16}$)alkyl, ($C_3$-$C_8$)alkenyl, ($C_3$-$C_8$)alkynyl, ($C_3$-$C_8$)cycloalkyl, alkyl substituted with ($C_1$-$C_6$)alkoxy or ($C_1$-$C_6$)halogenoalkyl, or represents a substituted phenyl, phenylacyl or benzyl group wherein the possible substituent on the phenyl, phenylacyl and benzyl group includes halogen, straight and branched ($C_1$-$C_8$)alkyl, ($C_1$-$C_8$)alkoxy, ($C_3$-$C_8$)alkenyl, ($C_3$-$C_8$)alkynyl. phenoxy, nitro, cyano and a five- or six-membered heterocyclic group containing one to four nitrogen atoms, and Hal is a halogen atom.

The compound of formula (IX) can be prepared from the compound of formula (VI') by means of a Sandmeyer reaction (cf. J. Chem. Soc. 87, 1946), in which the amine is diazotized with sodium nitrite and then reacted with a halogen compound such as bromine.

The compound of formula (IX) is then reacted with alcohol under basic condition to prepare the compound of formula(X).

In this reaction, a hydride such as potassium hydride, sodium hydride and the like, an alkoxide such as sodium methoxide, sodium ethoxide, potassium t-butoxide and the like, and inorganic base such as sodium bicarbonate, sodium carbonate, potassium carbonate and the like, etc., can be used as a base; an ether such as tetrahydrofuran, diethylether, etc., a halogenated hydrocarbon such as dichloromethane, dichloroethane, etc., a nitrile such as acetonitrile, etc., a polar solvent such as dimethylformamide, dimethylsulfoxide, dimethylacetamide, etc., and the like solvents can be used as a suitable solvent. The reaction can be carried out at the temperature between 0° C. and 120° C. and most preferably between 20° C. and 80° C.

The preparation of the compound of formula (I'') from the compound of formula (X) can be practiced in the same manner as outlined in the steps (b) and (c) for preparation of the compound of formula (I').

The compound of formula (I) wherein Y represents -SR⁵, said compound being represented by formula (I'''), can be prepared from a compound of formula (XII) following the same synthetic method as outlined in the steps (b) and (c) for preparation of the compound of formula (I'),

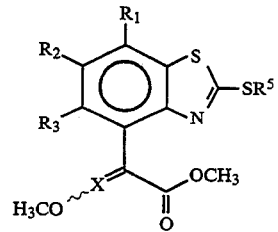

(I''')

(XII)

in which

R¹, R² and R³ independently of one another represent hydrogen, halogen, straight or branched ($C_1$-$C_8$)alkyl, ($C_1$-$C_8$)halogenoalkyl or ($C_1$-$C_8$)alkoxy, X represents N or CH, R⁵ represents hydrogen, straight and branched ($C_1$-$C_{16}$)alkyl, ($C_3$-$C_8$)alkenyl, ($C_3$-$C_8$)alkynyl, ($C_3$-$C_8$)cycloalkyl, alkyl substituted with ($C_1$-$C_6$)alkoxy, or ($C_1$-$C_6$)halogenoalkyl, or represents a substituted phenyl, phenylacyl or benzyl group wherein the possible substituent on the phenyl, phenylacyl or benzyl group includes halogen, straight and branched ($C_1$-$C_8$)alkyl, ($C_1$-$C_8$)alkoxy, ($C_3$-$C_8$)alkenyl, ($C_3$-$C_8$)alkynyl, phenoxy, nitro, cyano and a five- or six-membered heterocyclic group containing one to four nitrogen atoms, and Hal is a halogen atom.

The compound of formula (XII) which is required as starting compound for preparation of the compound of formula (I''') can be obtained following different two methods. In the first variant, the compound of formula (IX) as defined above is reacted with sodium hydrogensulfide to obtain a compound of formula (XI) which is then reacted with a halogenide compound under basic condition to obtain the compound of formula (XII). Alternatively, according to the second variant the compound of formula (XII) can be prepared by reacting a halogenide compound with sodium hydrogen-sulfide to obtain a thiol which is then reacted with the compound of formula (IX) as defined above under basic condition.

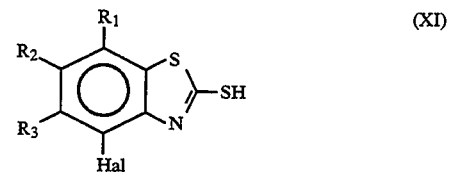

(XI)

In the above formula (XI), R¹, R², R³ and Hal are defined as previously described. In said two variants for preparing the compound of formula (XII), the reaction conditions are substantially identical to those previously described in the procedure for preparation of the compound of formula(X).

In preparing the compound of formula (XI), a suitable solvent which can be used is an ether such as tetrahydrofuran or diethyl ether, a halogenated hydrocarbon such as dichloromethane or dichloroethane, a nitrile such as acetonitrile, an alcohol such as methanol, ethanol; propanol, etc., a polar solvent such as dimethylformamide, dimethylsulfoxide, dimethylacetamide, etc., and the like solvents. The reaction can be practiced at the temperature between 0° C. and 120° C. and most preferably between 20° C. and 80° C.

In the first variant, the compound of formula (XII) can be obtained by reacting the compound of formula (XI) with a halogenide compound under basic condition. For this purpose, a suitable base which can be used is a hydride such as potassium hydride, sodium hydride, etc., an alkoxide such as sodium methoxide, sodium ethoxide, potassium dibutoxide, etc., an inorganic base such as sodium bicarbonate, sodium carbonate, potassium carbonate, etc., and the like bases ; and a suitable solvent which can be used is an ether such as tetrahydrofuran, diethylether, etc., a halogenated hydrocarbon such as dichloromethane, dichloroethane, etc., a nitrile such as acetonitrile, etc., a polar solvent such as dimethylformamide, dimethylsulfoxide, dimethylacetamide, etc., and the like solvents. The reaction can be carried out at the temperature between 0° C. and 150° C. and most preferably between 20° C. and 80° C.

The present invention will be more specifically illustrated by the following examples but it should be understood that the present invention is not limited to these examples in any manner.

Preparation 1

Synthesis of 4-methylphenylthiourea 10.7 g of 4-toluidine was added dropwise to 27% aqueous sulfuric acid solution which contains 5.4 g of sulfuric acid. After the reaction mixture was heated to 75° C., 8.4 g of ammonium thiocyanate in a solid state was slowly added thereto. Upon complete addition, the reaction mixture was stirred for 20 hours at 80° C. to 90° C. After adding toluene, the whole mixture was refluxed for one hour, cooled to room temperature and then adjusted to pH 7.5 to 8 by slowly adding ammonia water. The resulting white solid was filtered, washed once with each of water and toluene and then dried under reduced pressure to obtain the title compound as a white solid (Yield: 78.5%).

$^1$H NMR(CDCl$_3$): 2.34(3H, s), 6.2(2H, br s, —NH$_2$), 7.15(4H, q), 7.98(1H, br s, —NH—)

Preparation 2

Synthesis of 2-amino-6-methylbenzothiazole 15 ml of concentrated sulfuric acid was added to 8.3 g of the compound prepared in Preparation 1 and the temperature of the mixture was raised to 80° C. After 0.5 g of 48% hydrobromic acid was slowly added, the reaction mixture was stirred for 2 hours at 80° C. and then cooled to room temperature. The reaction solution was slowly introduced into cold water and then adjusted to pH9 to 10 by adding ammonia water. The whole mixture was stirred for one hour while heating at 70° C., and then cooled to room temperature. The mixture was extracted two times with dichloroethane and the combined extract was dried with anhydrous sodium sulfate and evaporated to obtain the title compound as a yellow solid (Yield: 84% ).

$^1$H NMR(CDCl$_3$): 2.40(3H, s), 5.5(2H, br s, —NH$_2$), 7.12(1H, d), 7.41(2H, t)

EXAMPLE 1

Synthesis of 2-amino-4-bromo-6-methylbenzothiazole 16.4 g of 2-amino-6-methylbenzothiazole was dissolved in 500 ml of chloroform. To this solution was added dropwise 16.0 g of bromine dissolved in 10 ml of chloroform at room temperature. The reaction mixture was stirred for 2 hours and then washed once with 10% aqueous sodium hydroxide solution and water, respectively. The organic layer was separated, dried with anhydrous sodium sulfate and then evaporated to obtain the title compound in the yield of 92%.

$^1$H NMR(CDCl$_3$): 2.41(3H, s), 5.94(2H, br s, —NH2), 7.32(2H, s)

EXAMPLE 2

Synthesis of 2-(N,N'-dimethyl)amino-4-bromo-6-methylbenzothiazole 2.43 g of the compound obtained in Example 1, 0.82 g of sodium hydroxide, 2.88 g of methyl iodide and 30 ml of acetonitrile were introduced into a reaction vessel and the reaction mixture was refluxed for one hour. Acetonitrile was then evaporated under reduced pressure and the residue was extracted with diethylether and water. The organic layer was separated, dried with anhydrous sodium sulfate, evaporated and then subjected to column chromatography to separate the desired product as a yellow solid in the yield of 66%.

$^1$H NMR(CDCl$_3$):2.35(3H, s), 3.21(6H, s), 7.30(2H, s)

EXAMPLE 3

Synthesis of methyl[2-(N,N'-dimethyl)amino-6-methylbenzothiazol-4-yl]keto acetate A solution of 0.55 g of 2-(N,N'-dimethyl)amino-6-methylbenzothiazole in 5 ml of diethylether was slowly added dropwise to 10 ml of diethylether solution of n-butyl lithium (1.26 ml as 2.5M hexane solution) at −78° C. and the mixture was stirred for 30 minutes. 5 ml of diethylether solution containing 0.22 g of dimethyloxalate was slowly added dropwise thereto and the temperature was raised gradually to room temperature. The whole mixture was washed with ammonium chloride solution and the separated organic layer was dried with anhydrous sodium sulfate and then evaporated to obtain the title compound as a yellow liquid in the yield of 77%.

$^1$H NMR(CDCl$_3$):2.41(3H, s), 3.20(6H, s), 3.96(3H, s), 7.63(1H, s), 7.74(1H, s)

EXAMPLE 4

Synthesis of (E,Z)-methyl 2-[2-(N,N'-dimethyl)amino-6-methylbenzothiazol-4-yl]-2-methoxyiminoacetate

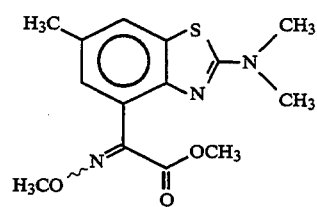

0.28 g of the compound prepared in Example 3, 0.09 g of methoxylamine hydrochloride, 0.08 g of potassium carbonate and 1 ml of ethanol were introduced into a reaction vessel and the mixture was refluxed for one hour. After cooling, ethanol was evaporated under reduced pressure and the residue was extracted with ethyl acetate and water. The ethyl acetate layer was separated, dried with anhydrous sodium sulfate, evaporated and then subjected to column chromatography to obtain E-isomer and Z-isomer of the title compound in the yield of 15% and 68%, respectively.

E-isomer $^1$H NMR (CDCl$_3$):2.39(3H, s), 3.15(6H, s), 3.92(3H, s), 4.05(3H, s), 7.43(1H, s), 7.57(1H, s)

Z-isomer $^1$H NMR(CDCl$_3$): 2.40(3H, s), 3.19(6H, s), 3.88(3H, s), 4.10(3H, s), 7.42(1H, s), 7.61(1H, s)

EXAMPLE 5

Synthesis of (E,Z)-methyl 2-[2-(N,N'-dimethyl)amino-6-methylbenzothiazol-4-yl]-3-methoxypropenoate

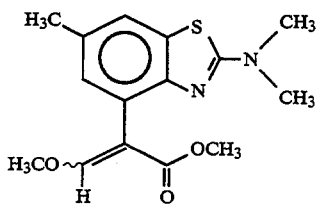

To 30 ml of tetrahydrofuran solution containing 3.4 g of methoxymethyltriphenylphosphonium chloride was added 0.9 g of potassium t-butoxide at room temperature and the mixture was stirred for 30 minutes. 10 ml of tetrahydrofuran solution containing 1.4 g of methyl [2-(N,N'-dimethyl)amino-6-methylbenzothiazol-4-yl]keto acetate was added dropwise thereto and then the mixture was refluxed for 2 hours. After cooling, tetrahydrofuran was evaporated under reduced pressure and the residue was extracted with ethyl acetate and water. The ethyl acetate layer was separated, dried with anhydrous sodium sulfate, evaporated and then subjected to column chromatography to obtain E-isomer and Z-isomer of the title compound in the yield of 12% and 58%, respectively.

E-isomer $^1$H NMR(CDCl$_3$): 2.38(3H, s), 3.17(6H, s), 3.71(3H, s), 3.89(3H, s), 6.88(1H, s), 6.94(1H, s), 7.30(1H, s)

Z-isomer $^1$H NMR(CDCl$_3$): 2.37(3H, s), 3.15(6H, s), 3.68(3H, s), 3.82(3H, s), 7.05(1H, s), 7.29(1H, s), 7.52(1H, s)

EXAMPLE 6

Synthesis of 2,4-dibromo-6-methylbenzothiazole 4.7 g of 2-amino-4-bromo-6-methylbenzothiazole, 14 ml of 48% bromic acid solution and 10 g of bromine were introduced into a reaction vessel while keeping the temperature at 10° C. To this mixture was slowly added dropwise 10 ml of aqueous solution containing 3.5 g of sodium nitrite at 0° C. and the whole mixture was stirred for 2 hours. Then, 15 ml of 40% sodium hydroxide solution was slowly added dropwise while keeping the temperature below 20° C. and the reaction mixture was stirred for one hour and extracted with diethyl ether. The extract was dried with anhydrous sodium sulfate and evaporated to obtain the title compound in the form of transparent liquid (Yield: 91%).

$^1$H NMR(CDCl$_3$): 7.29(2H, s), 2.44(3H, s)

EXAMPLE 7

Synthesis of 4-bromo-2-allylmercapto-6-methylbenzothiazole 1.20 g of allyl bromide, 0.7 g of sodium hydrogensulfide and 10 ml of dichloromethane were introduced into a reaction vessel and then the mixture was refluxed for one hour and washed with water under cooling. The dichloromethane layer was separated, dried with anhydrous sodium sulfate and distilled under reduced pressure to remove dichloromethane to obtain 1.0 g of allyl mercaptan.

1.0 g of allyl mercaptan prepared above, 3.1 g of 2,4-dibromo-6-methyl-benzothiazole, 0.4 g of sodium hydroxide, 10 ml of tetrahydrofuran and 10 ml of water were mixed together and the obtained mixture was stirred for 3 hours at room temperature and then extracted with ethyl acetate. The extract was dried with anhydrous sodium sulfate and evaporated to obtain the title compound in a liquid state (Yield: 92.5%).

$^1$H NMR(CDCl$_3$): 2.41(3H, s), 4.00(2H, d), 5.20(1H, d), 5.42(1H, d), 6.01(1H, m), 7.44(2H, d)

EXAMPLE 8

Synthesis of 4-bromo-2-mercapto-6-methylbenzothiazole 3.1 g of 2,4-dibromo-6-methylbenzothiazole, 1.0 g of sodium hydrogensulfide and 30 ml of methanol were mixed and the obtained mixture was refluxed for one hour, cooled to room temperature and then distilled under reduced pressure to remove methanol. The residue was extracted with dichloromethane by adding water and dichloromethane. The dichloromethane layer was dried with anhydrous sodium sulfate and evaporated to obtain the title compound in a solid state (Yield: 84%).

$^1$H NMR(CDCl$_3$): 2.41(3H, s), 7.18(1H, s), 7.27(1H, s)

EXAMPLE 9

Synthesis of 4-bromo-2-n-butylmercapto-6-methylbenzothiazole

To 10 ml of tetrahydrofuran solution containing 0.52 g of 4-bromo-2-mercapto-6-methylbenzothiazole was added 50 mg of sodium hydride at 0° C. After adding 0.28 g of n-bromobutane, the whole mixture was refluxed for 2 hours, distilled under reduced pressure to remove tetrahydrofuran and then extracted with ethyl acetate by adding water and ethyl acetate. The ethyl acetate layer was dried with anhydrous sodium sulfate and evaporated under reduced pressure to obtain the title compound in a yellow liquid state (Yield: 66%).

$^1$H NMR(CDCl$_3$): 0.95(3H, t), 1.51(2H, m), 1.82(2H, m), 2.41(3H, s), 3.33(2H, t), 7.44(2H, d)

EXAMPLE 10

Synthesis of methyl (2-n-butylmercapto-6-methylbenzothiazol-4-yl)keto acetate 0.8 ml of t-butyl lithium solution was slowly added dropwise at −78° C. to 10 ml of diethyl ether solution containing 0.40 g of 4-bromo-2-n-butyl-mercapto-6-methylbenzothiazole, and the mixture was stirred for 30 minutes. To this mixture was added dropwise 10 ml of diethyl ether solution of dimethyloxalate (0.15 g) at −78° C. Then, the reaction mixture was stirred for one hour and the temperature was raised to room temperature. The reaction solution was washed with ammonium chloride solution and the organic layer was separated, dried with anhydrous sodium sulfate, evaporated and then subjected to column chromatography to obtain the title compound in the yield of 46%.

$^1$H NMR(CDCl$_3$): 0.97(3H, t), 1.50(2H, m), 1.79(2H, m), 2.50(3H, s), 3.33(2H, t), 3.98(3H, s), 7.81(2H, d)

EXAMPLE 11

Synthesis of (E,Z)-methyl-2-(2-n-butylmercapto-6-methylbenzothiazol-4-yl)-2-methoxyimino acetate

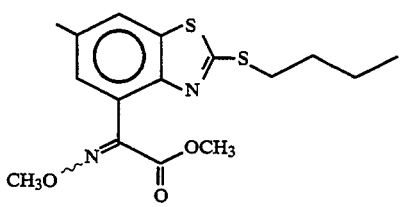

0.5 g of methyl (2-n-butylmercapto-6-methylbenzothiazol-4-yl) keto acetate was mixed with 0.13 g of methoxylamine hydrochloride, 0.2 g of potassium carbonate and 10 ml of ethanol, and then the mixture was refluxed for one hour and distilled under reduced pressure to remove ethanol. The residue was extracted with ethyl acetate by adding water and ethyl acetate. The ethyl acetate layer was dried with anhydrous sodium sulfate, evaporated and then subjected to column chromatography to obtain E-isomer and Z-isomer of the title compound in the yield of 28% and 63%, respectively.

E-isomer $^1$H NMR(CDCl$_3$): 0.95(3H, t), 1.48(2H, m), 1.78(2H, m), 2.47(3H, s), 3.29(2H, t), 3.80(3H, s), 4.09(3H, s), 7.24(1H, s), 7.59(1H, s)

Z-isomer $^1$H NMR(CDCl$_3$): 0.96(3H, t), 1.49(2H, m), 1.76(2H, m), 2.45(3H, s), 3.31(2H, t), 3.90(3H, s), 4.09(3H, s), 7.58(1H, s), 7.68(1H, s)

Typical compounds of formula (I) according to the present invention are listed in the following Table 1 and Table 2.

TABLE 1

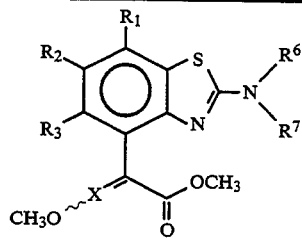

| Compound No. | R$^1$ | R$^2$ | R$^3$ | X | R$^6$ | R$^7$ | $^1$H NMR(CDCl$_3$) δ | Isomer |
|---|---|---|---|---|---|---|---|---|
| 1 | H | CH$_3$ | H | N | CH$_3$ | CH$_3$ | see Example 4 | E |
| 2 | H | CH$_3$ | H | N | CH$_3$ | CH$_3$ | see Example 4 | Z |
| 3 | H | CH$_3$ | H | C | CH$_3$ | CH$_3$ | see Example 5 | E |
| 4 | H | CH$_3$ | H | C | CH$_3$ | CH$_3$ | see Example 5 | Z |
| 5 | H | CH$_3$ | H | C | CH$_2$CH=CH$_2$ | CH$_2$CH=CH$_2$ | 2.37(3H, s), 3.71(3H, s), 3.90 (3H, s), 4.10(4H, d), 5.22(4H, 2d), 5.82(2H, m), 6.88(1H, s), 6.94(1H, s), 7.30(1H, s) | E |
| 6 | H | CH$_3$ | H | C | CH$_2$CH=CH$_2$ | CH$_2$CH=CH$_2$ | 2.36 (3H, s), 3.66 (3H, s), 3.84 (3H, s), 4.08(4H, d), 5.22(4H, 2d), 5.82(2H, m), 7.01(1H, s), 7.30 (1H, s), 7.52(1H, s) | Z |
| 7 | H | CH$_3$ | H | N | n-butyl | n-butyl | 0.96(6H, m), 1.50(4H, m), 1.71 (4H, d), 2.35(3H, s), 2.93(2H, t), 3.30(2H, m), 3.69(3H, s), 3.84 (3H, s), 6.82(1H, s), 6.95(1H, s), 7.29(1H, s) | E |
| 8 | H | CH$_3$ | H | N | n-butyl | n-butyl |  | Z |
| 9 | H | CH$_3$ | H | N | CH$_2$C$_6$H$_5$ | H | 2.34(3H, s), 3.89(3H, s), 4.06 (3H, s), 4.81(2H, s), 5.50(1H, brs), 7.30(6H, m), 7.40(1H, s) | E |
| 10 | H | CH$_3$ | H | N | CH$_2$C$_6$H$_5$ | H |  | Z |

TABLE 1-continued

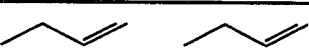

| Compound No. | R¹ | R² | R³ | X | R⁶ | R⁷ | ¹H NMR(CDCl₃) δ | Isomer |
|---|---|---|---|---|---|---|---|---|
| 11 | H | F | H | N | CH₂CH=CHCH₃ | CH₂CH=CHCH₃ | 3.84(3H, s), 4.04(3H, s), 4.08 (4H, d), 5.25(4H, 2d), 5.80(2H, m) 7.20(1H, 2d), 7.32(1H, 2d) | E |
| 12 | H | F | H | N | CH₂CH=CHCH₃ | CH₂CH=CHCH₃ | 3.89(3H, s), 4.04(3H, s), 4.08 (4H, 2d), 5.25(4H, 2d), 5.82(2H, m), 7.33(1H, 2d), 7.50(1H, 2d) | Z |
| 13 | F | F | F | N | CH₃ | CH₃ | 3.18(6H, s), 3.95(3H, s), 4.09 (3H, s) | E |
| 14 | F | F | F | N | CH₃ | CH₃ | 3.19(6H, s), 3.97(3H, s), 4.09 (3H, s) | Z |
| 15 | H | Cl | H | C | CH₃ | CH₃ | 3.19(6H, s), 3.72(3H, s), 3.92 (3H, s), 6.86(1H, s), 6.97(1H, s), 7.35(1H, s) | E |
| 16 | H | Cl | H | C | CH₃ | CH₃ | 3.19(6H, s), 3.70(3H, s), 3.89 (3H, s), 7.01(1H, s), 7.30(1H, s), 7.50(1H, s) | Z |
| 17 | H | CH₃ | H | N | C(=O)Ph | H | | E |
| 18 | H | CH₃ | H | N | C(=O)Ph | H | | Z |
| 19 | H | CH₃ | H | N | morpholine (—N(CH₂CH₂)₂O) | | 2.41(3H, s), 3.65(4H, t), 3.80 (4H, t), 3.89(3H, s), 4.07(3H, s), 7.46(1H, s), 7.58(1H, s) | Z |

TABLE 2

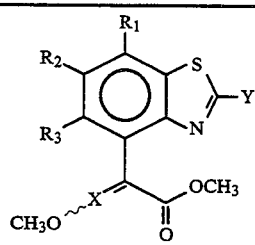

| Compound No. | R₁ | R₂ | R₃ | X | Y | ¹H NMR(CDCl₃) δ | Isomer |
|---|---|---|---|---|---|---|---|
| 20 | H | CH₃ | H | N | —OCH₃ | 2.48(3H, s), 3.86(3H, s), 4.08(3H, s), 4.11(3H, s), 7.24(1H, s), 7.48(3H, s) | E |
| 21 | H | CH₃ | H | N | —OCH₃ | 2.43(3H, s), 3.93(3H, s), 4.05(3H, s), 4.12(3H, s), 7.50(1H, s), 7.66(1H, s) | Z |
| 22 | H | CH₃ | H | N | —OCH₂CH₃ | 1.19(3H, t), 2.44(3H, s), 3.87(3H, s), 4.08(3H, s), 4.40(2H, q), 7.25(1H, s), 7.49(1H, s) | E |
| 23 | H | CH₃ | H | N | —OCH₂CH₃ | 1.20(3H, t), 2.44(3H, s), 3.90(3H, s), 4.08(3H, s), 4.41(2H, q), 7.49(1H, s), 7.66(1H, s) | Z |

TABLE 2-continued

| Compound No. | R₁ | R₂ | R₃ | X | Y | ¹H NMR(CDCl₃) δ | Isomer |
|---|---|---|---|---|---|---|---|
| 24 | H | CH₃ | H | N |  | 1.02(3H, t), 1.82(2H, m), 2.43(3H, s), 3.85(3H, s), 4.08(3H, s), 4.43(2H, t), 7.28(1H, s), 7.48(1H, s) | E |
| 25 | H | CH₃ | H | N |  | 1.03(3H, t), 1.83(2H, m), 2.41(3H, s), 3.91(3H, s), 4.06(3H, s), 4.43(2H, t), 7.48(1H, s), 7.64(1H, s) | Z |
| 26 | H | CH₃ | H | N |  | 2.43(3H, s), 3.83(3H, s), 4.08(3H, s), 4.95(2H, d), 5.25–5.48(2H, q), 6.04 (1H, m), 7.23(1H, s), 7.47(1H, s) | E |
| 27 | H | CH₃ | H | N |  | 2.43(3H, s), 3.90(3H, s), 4.09(3H, s), 4.98(2H, d), 5.31–5.50(2H, q), 6.10 (1H, m), 7.49(1H, s), 7.64(1H, s) | Z |
| 28 | H | CH₃ | H | N |  | 1.89(3H, s), 2.43(3H, s), 3.8H(3H, s), 4.08(3H, s), 5.04(2H, q), 7.24(1H, s), 7.48(1H, s) | E |
| 29 | H | CH₃ | H | N |  | 1.88(3H, s), 2.43(3H, s), 3.92(3H, s), 4.08(3H, s), 5.05(2H, q), 7.48(1H, s), 7.65(1H, s) | Z |
| 30 | H | CH₃ | H | N | —O—(CH₂)₁₁—CH₃ | 0.89(3H, t), 1.20–1.50(18H, m), 1.81 (2H, m), 2.42(3H, s), 3.85(3H, s), 4.08(3H, s), 4.46(2H, t), 7.22(1H, s), 7.48(1H, s) | E |
| 31 | H | CH₃ | H | N | —O—(CH₂)₁₁—CH₃ | 0.89(3H, t), 1.20–1.50(18H, m), 1.81 (2H, m), 2.42(3H, s), 3.91(3H, s), 4.08(3H, s), 4.48(2H, t), 7.48(1H, s), 7.64(1H, s) | Z |
| 32 | H | CH₃ | H | N |  | 2.46(3H, s), 3.78(3H, s), 4.07(3H, s), 7.25–7.53(7H, m) | E |
| 33 | H | CH₃ | H | N |  | 2.47(3H, s), 3.40(3H, s), 4.06(3H, s), 7.25–7.73(7H, m) | Z |
| 34 | H | CH₃ | H | N |  | 2.46(3H, s), 3.87(3H, s), 4.04(3H, s), 7.28(1H, s), 7.29–7.41(4H, q), 7.52 (1H, s) | E |
| 35 | H | CH₃ | H | N |  | 2.47(3H, s), 3.42(3H, s), 4.03(3H, s), 7.38(4H, q), 7.52(1H, s)7.71(1H, s) | Z |
| 36 | H | CH₃ | H | N |  | 2.24(3H, s), 2.45(3H, s), 3.74(3H, s), 4.04(3H, s), 7.25(6H, m), 7.50(1H, s) | E |

TABLE 2-continued

| Compound No. | R₁ | R₂ | R₃ | X | Y | ¹H NMR(CDCl₃) δ | Isomer |
|---|---|---|---|---|---|---|---|
| 37 | H | CH₃ | H | N | 2-methylphenoxy | 2.25(3H, s), 2.42(3H, s), 3.30(3H, s), 4.02(3H, s), 7.25(5H, m), 7.51(1H, s), 7.70(1H, s) | Z |
| 38 | H | CH₃ | H | N | 2,6-dimethylphenoxy | 2.24(6H, s), 2.46(3H, s), 3.72(3H, s), 4.05(3H, s), 7.10(3H, m), 7.25(1H, s), 7.49(1H, s) | E |
| 39 | H | CH₃ | H | N | 2,6-dimethylphenoxy | 2.24(6H, s), 2.43(3H, s), 3.22(3H, s), 4.01(3H, s), 7.06(3H, m), 7.50(1H, s), 7.68(1H, s) | Z |
| 40 | H | CH₃ | H | N | 3-isopropylphenoxy | 1.36(6H, d), 2.43(3H, s), 2.92(1H, m), 3.79(3H, s), 4.06(3H, s), 7.10–7.38 (5H, m), 7.50(1H, s) | E |
| 41 | H | CH₃ | H | N | 3-isopropylphenoxy | 1.29(6H, d), 2.43(3H, s), 3.95(1H, m), 3.35(3H, s), 4.04(3H, s), 7.13(3H, m), 7.32(1H, m), 7.51(1H, s), 7.72(1H, s) | Z |
| 42 | H | CH₃ | H | N | 3,5-dimethoxyphenoxy | 2.46(3H, s), 3.75(3H, s), 3.80(3H, s), 4.06(3H, s), 6.78–6.97(3H, m), 7.27 (2H, m), 7.52(1H, s) | E |
| 43 | H | CH₃ | H | N | 3,5-dimethoxyphenoxy | 2.44(3H, s), 3.42(3H, s), 3.83(3H, s), 4.04(3H, s), 6.78–6.96(3H, m), 7.31 (1H, t), 7.51(1H, s), 7.73(1H, s) | Z |
| 44 | H | CH₃ | H | N | 3-allyloxy-5-methoxyphenoxy | 2.45(3H, s), 3.79(3H, s), 4.08(3H, s), 4.53(2H, d), 5.25–5.45(2H, q), 6.02 (1H, m), 6.78–6.96(3H, m), 7.26(2H, m), 7.51(1H, s) | E |
| 45 | H | CH₃ | H | N | 3-allyloxy-5-methoxyphenoxy | 2.42(3H, s), 3.45(3H, s), 4.06(3H, s), 4.53(2H, d), 5.20–5.44(2H, q), 6.02 (1H, m), 6.77–6.97(3H, m), 7.30(1H, t), 7.52(1H, s), 7.72(1H, s) | Z |

TABLE 2-continued

[Structure: benzothiazole with R1, R2, R3 substituents on benzene ring, Y on thiazole, and —C(=X-OCH3)—C(=O)OCH3 group; CH3O~X]

| Compound No. | R1 | R2 | R3 | X | Y | 1H NMR(CDCl3) δ | Isomer |
|---|---|---|---|---|---|---|---|
| 46 | H | CH3 | H | N | [3-methoxy-isopropoxyphenyl] | 1.32(6H, d), 2.45(3H, s), 3.80(3H, s), 4.07(3H, s), 4.51(1H, m), 6.76–6.96 (3H, m), 7.27(2H, m), 7.51(1H, s) | E |
| 47 | H | CH3 | H | N | [3-methoxy-isopropoxyphenyl] | 1.32(6H, d), 2.45(3H, s), 3.49(3H, s), 4.06(3H, s), 4.54(1H, m), 6.76–6.96 (3H, m), 7.30(1H, t), 7.52(1H, s), 7.72 (1H, s) | Z |
| 48 | H | CH3 | H | N | [3-methoxyphenoxy-phenyl] | 2.43(3H, s), 3.79(3H, s), 4.08(3H, s) 6.85–7.19(6H, m), 7.26–7.45 (4H, m), 7.50(1H, s) | E |
| 49 | H | CH3 | H | N | [3-methoxyphenoxy-phenyl] | 2.44(3H, s), 3.47(3H, s) 4.06(3H, s), 6.84–7.20(6H, m) 7.25–7.45(3H, m), 7.51(1H, s), 7.71(1H, s) | Z |
| 50 | H | CH3 | H | N | [3-methoxyphenoxy-pyrimidinyl] | 2.45(3H, s), 3.80(3H, s), 4.07(3H, s), 6.88(4H, s), 7.28(2H, m), 7.81(1H, s), 8.65(2H, d) | E |
| 51 | H | CH3 | H | N | [3-methoxyphenoxy-pyrimidinyl] | 2.45(3H, s), 3.45(3H, s), 4.06(3H, s), 6.84(4H, m), 7.30(1H, t), 7.51(1H, s), 7.70(1H, s), 8.66(2H, d) | Z |
| 52 | H | CH3 | H | N | —SCH3 | 2.46(3H, s), 2.72(3H, s), 3.84(3H, s), 4.09(3H, s), 7.26(1H, s), 7.59(1H, s), | E |
| 53 | H | CH3 | H | N | —SCH3 | 2.46(3H, s), 2.75(3H, s), 3.92(3H, s), 4.10(3H, s), 7.24(1H, s), 7.60(1H, s) | Z |
| 54 | H | CH3 | H | N | —S-allyl | 2.47(3H, s), 3.84(3H, s), 3.92(2H, d), 4.08(3H, s), 5.15(1H, d), 5.32(1H, d), 6.00(1H, m), 7.24(1H, s), 7.60(1H, s) | E |
| 55 | H | CH3 | H | N | —S-allyl | 2.47(3H, s), 3.91(3H, s), 3.93(2H, d), 4.09(3H, s), 5.17(1H, d), 5.37(1H, d) 6.00(1H, m), 7.60(1H, s), 7.70(1H, s) | Z |
| 56 | H | CH3 | H | N | —S-ethyl | 1.3(3H, t), 2.45(3H, s), 3.27(2H, q), 3.85(3H, s), 4.09(3H, s), 7.24(1H, s), 7.58(1H, s) | E |
| 57 | H | CH3 | H | N | —S-ethyl | 1.3(3H, t), 2.45(3H, s), 3.27(2H, q), 3.88(3H, s), 4.09(3H, s), 7.58(1H, s), 7.68(1H, s) | Z |
| 58 | H | CH3 | H | N | —S-pentyl | see Example 11 | E |
| 59 | H | CH3 | H | N | —S-pentyl | see Example 11 | Z |
| 60 | H | CH3 | H | N | —S-heptyl | 0.90(3H, t), 1.22–1.50(6H, m), 1.78 (2H, m), 2.46(3H, s), 3.28(2H, t), 3.85 (3H, s), 4.08(3H, s), 7.24(1H, s), 7.58 (1H, s) | E |

TABLE 2-continued

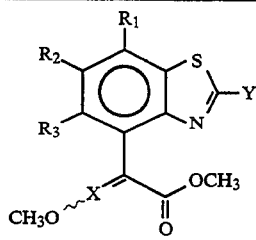

| Compound No. | $R_1$ | $R_2$ | $R_3$ | X | Y | $^1$H NMR(CDCl$_3$) δ | Isomer |
|---|---|---|---|---|---|---|---|
| 61 | H | CH$_3$ | H | N | —S-heptyl | 0.89(3H, t), 1.23–1.52(6H, m), 1.77 (2H, m), 2.46(3H, s), 3.30(2H, t), 3.91(3H, s), 4.08(3H, s), 7.59(1H, s), 7.69(1H, s) | Z |
| 62 | H | CH$_3$ | H | N | —S-isopropyl | 1.45(6H, d), 2.46(3H, s), 3.84(3H, s), 4.07(3H, s), 4.08(1H, m), 7.24(1H, s), 7.59(1H, s) | E |
| 63 | H | CH$_3$ | H | N | —S-isopropyl | 1.49(6H, d), 2.44(3H, s), 3.89(3H, s), 4.07(1H, m), 4.09(3H, s), 7.60(1H, s), 7.68(1H, s) | Z |
| 64 | H | CH$_3$ | H | N | —S-isobutyl | 1.10(6H, d), 2.11(1H, m), 2.42(3H, s), 3.21(2H, d), 3.87(3H, s), 4.08(3H, s), 7.25(1H, s), 7.59(1H, s) | E |
| 65 | H | CH$_3$ | H | N | —S-CH$_2$CH=CHCH$_3$ | 1.70(3H, d), 2.46(3H, s), 3.87(3H, s), 4.00(2H, d), 4.10(3H, s), 5.55–5.90 (2H, m), 7.25(1H, s), 2.60(1H, s) | E |
| 66 | H | CH$_3$ | H | N | —S-CH$_2$CH=CHCH$_3$ | 1.72(3H, d), 2.46(3H, s), 3.89(3H, s), 3.90(2H, d), 4.10(3H, s), 5.55–5.90 (2H, m), 7.60(1H, s), 7.70(1H, s) | Z |
| 67 | H | CH$_3$ | H | N | —S-cyclohexyl | 1.25–1.65(6H, m), 1.79(2H, m), 2.13 (2H, m), 2.45(3H, s), 3.82(3H, s), 3.85 (1H, m), 4.08(3H, s), 7.24(1H, s), 7.57 (1H, s) | E |
| 68 | H | CH$_3$ | H | N | —S-cyclohexyl | 1.20–1.65(6H, m), 1.80(2H, m), 2.15 (2H, m), 2.44(3H, s), 3.89(8H, s), 3.90 (1H, m), 4.08(3H, s), 7.59(1H, s), 7.66 (1H, s) | Z |
| 69 | H | CH$_3$ | H | N | —S-CH$_2$-Ph | 2.46(3H, s), 3.84(3H, s), 4.07(3H, s) 4.53(2H, s), 7.28(5H, m), 7.26(1H, s), 7.59(1H, s) | E |
| 70 | H | CH$_3$ | H | N | —S-CH$_2$-Ph | 2.50(3H, s), 3.85(3H, s), 4.10(3H, s) 4.59(2H, s), 7.35(5H, m), 7.60(1H, s), 7.71(1H, s) | Z |
| 71 | H | F | H | N | —S-CH$_2$-Ph | 3.86(3H, s), 4.10(3H, s), 4.55(2H, s), 7.19(1H, d), 7.30(5H, m), 7.36(1H, d) | E |
| 72 | H | F | H | N | —S-CH$_2$-Ph | 3.88(3H, s), 4.06(3H, s), 4.59(2H, s), 7.39(6H, m), 7.50(1H, d) | Z |

TABLE 2-continued

[Structure: benzothiazole with R1, R2, R3 substituents on benzene ring, connected to C(=NOCH3 or similar)C(=O)OCH3 group with X and Y substituents, Y on thiazole position]

| Compound No. | R₁ | R₂ | R₃ | X | Y | ¹H NMR(CDCl₃) δ | Isomer |
|---|---|---|---|---|---|---|---|
| 73 | F | F | F | N | –S–C₆H₅ | 3.88(3H, s), 4.11(3H, s), 7.33(5H, m) | E |
| 74 | H | CH₃ | H | N | –S–C₆H₅ | 2.44(3H, s), 3.86(3H, s), 4.08(3H, s), 7.22(1H, s), 7.47(1H, s), 7.46–7.71 (5H, m) | E |
| 75 | H | CH₃ | H | N | –S–C₆H₅ | 2.44(3H, s), 3.85(3H, s), 4.09(3H, s), 7.45–7.72(7H, m) | Z |

Biological examples

The microbicidal effect of the active compound according to the present invention was examined using the following phythopathogenic organisms.

*Pyricularia oryzae* (PO): rice blast (RCB)
*Rhizoctonia solani* (RS): rice sheath blight (RSB)
*Botrytis cinerea* (BC): cucumber gray mold (CGM)
*Phytophthora infestans* (PI): tomato late blight (TLB)
*Puccinia recondita* (PR): wheat leaf rust (WLR)
*Erysiphe graminis* (EG): barley powdery mildew (BPM)

To determine the preventive effect of the compound according to the present invention against phythopathogenic organisms, the active compound was dissolved in 10% acetone solution and then Tween-20 was added in the concentration of 250 ppm to prepare a suitable test preparation of active compound. Host plants in a certain size were sprayed with the test preparation in an amount of 50 ml per each plant on their leaves. The plants were remained for 24 hours at room temperature to volatilize the solvent and water and then were inoculated with phythopathogenic organisms as prepared below. All tests were repeated two times.

Test 1

Fungicidal effect on rice blast causative organism

Rice blast causative organism(*Pyricularia oryzae*) was inoculated on rice bran-agar medium (Rice Ploish 20 g, Dextrose 10 g, Agar 15 g, D.W. 1 L) and incubated in an incubator at 26°±2° C. for 2 Weeks. The surface of medium on which organisms were grown was scraped with a rubber sweeper to remove aerial mycelium. The medium was then placed on a shelf (25° C. to 28° C.) lighted by fluorescent lamp for 48 hours to develop spores. The developed conidiospore was added to sterilized distilled water to prepare a conidia suspension ($10^6$ spores/ml) and 3-4 leaves stage rice plants (variants: Nak Dong) sensitive to rice blast was sprayed with the conidia suspension prepared above until dripping wet.

The inoculated rice plants were placed in a humidity chamber under dark for 24 hours and then in a humidistat at temperature of 26°±2° C. and a relative humidity of 90% and over for 5 days. Thereafter, the infected area on rice plants was measured on a fully developed leaf just below the top leaf of 3–4 leaves stage rice plant. The fungicidal effect of the active compound was determined from the measured infected area by comparing with the standard infected area.

Test 2

Fungicidal effect on rice sheath blight causative organism

An appropriate amount of wheat bran was introduced into a 1 L incubation bottle, sterilized and then incubated with a fragment of potato-agar medium on which rice sheath blight causative organism (*Rhizoctonia solani* AG-1) was grown for 3 days. The incubated mycelium mass was ground in a suitable size. A pot (5 cm) in which 2-3 leaves stage rice plants (variants: Nak Dong) were grown was inoculated uniformly with the mycelium and incubated in a humidity chamber (28°±1° C.) and then placed in a humidistat at relative humidity of 80% and over for 5 days. Thereafter, the occurrence of plant disease was determined by measuring the infected area on the sheath of 2-3 leaves stage rice seedling which is then compared with a comparative table for the ratio between the total sheath area and the infected area.

Test 3

Fungicidal effect on cucumber gray mold causative organism

Gray mold causative organism (*Botrytis cinerea* KCI) isolated from cucumber was inoculated on potato-agar medium (PDA). This plate was incubated in an incubator at 25° C. under dark for 15 days to develop spores.

The spores developed on the medium were collected and filtered with a gauze to harvest the spore which was then suspended in a sterilized water in the concentration of $10^6$ spores/ml.

One leaf stage cucumber was sprayed with the spore suspension prepared above and then placed in a humidity chamber at 20° C. for 3 days. Thereafter, the infected area on one leaf of cucumber was measured.

Test 4

Fungicidal effect on tomato late blight causative organism

A V-8 juice agar medium (V-8 juice 200 ml, $CaCO_3$ 4.5 g, agar 15 g, distilled water 800 ml) was inoculated with tomato late blight causative organism (*Phytophthora infestans*) and placed at 20° C. under light for 16 hours and then under dark for 8 hours, and incubated for 14 days to develop spores. A sterilized distilled water was added to the medium and shaked to remove zoosporangium from the lawn. The zoosporangium was filtered through 4-fold scrap of cloth and then adjusted in the concentration of $1 \times 10^5$ zoospore/ml to prepare an inoculum. Tomato seedlings were sprayed with the inoculum and then placed in a humidity chamber at 20° C. for one week and subsequently in a humidistat at 20° C. and 80% and over relative humidity for 4 days. Thereafter, the infected area on the first and second leaves of tomato was measured.

Test 5

Fungicidal effect on wheat leaf rust causative organism

Wheat leaf-rust causative organism (*Puccinia recondita*) was subcultured directly on plants in a laboratory and used as a test organism. To subculture the organism and determine the fungicidal effect of active compound, 15 grains of wheat seed (variants: Eunpa) were sowed in a disposable pot (diameter: 6.5 cm) and then cultivated in a greenhouse to one-leaf stage, which was then placed in a humidity chamber at 20° C. for one day and transferred to a humidistat at 20° C. and 70% relative humidity. The organism was inoculated on wheat plants to induce infection. Evaluation was carried out 10 days after the inoculation by measuring the infected area.

Test 6

Fungicidal effect on barley powdery mildew causative organism

Barley powdery mildew causative organism (*Erysiphe graminis* f.sp. *hordei*) was subcultured in a laboratory and used as a test organism. To subculture the organism and determine the fungicidal effect of active compound, 15 grains of barley seed (variants: Dongbori No. 1) were sowed in a pot (diameter: 6.5 cm) and then cultivated in a greenhouse to one-leaf stage, on which the spore of powdery mildew causative organism was inoculated to induce infection. The inoculated bareley plants were transferred to a humidistat at 22° to 24° C. and 50% relative humidity and placed therein for 7 days. Thereafter, the infected area was measured.

The fungicidal effect of each tested active compound at the concentration of 250 ppm was graded on the basis of the following criteria. The result is listed in the following Table 3.

TABLE 3

Fungicidal effect of the compound of formula (I)

Inhibition

TABLE 3-continued

Fungicidal effect of the compound of formula (I)

| rate | Grade |
|---|---|
| ≧90% | A |
| 60–89% | B |
| ≦59% | C |

| Compound No. | RCB | RSB | CGM | TLB | WLR | BPM |
|---|---|---|---|---|---|---|
| 1 | B | C | C | C | B | B |
| 2 | B | C | C | C | A | B |
| 3 | B | C | C | C | A | A |
| 4 | C | C | C | C | A | B |
| 5 | B | C | C | C | A | B |
| 6 | C | C | C | C | A | B |
| 7 | B | C | C | C | C | B |
| 8 | C | C | C | C | C | B |
| 9 | — | — | — | — | — | — |
| 10 | — | — | — | — | — | — |
| 11 | C | C | B | C | B | A |
| 12 | C | C | B | C | B | A |
| 13 | B | C | C | C | B | A |
| 14 | B | C | C | C | B | A |
| 15 | — | — | — | — | — | — |
| 16 | — | — | — | — | — | — |
| 17 | — | — | — | — | — | — |
| 18 | — | — | — | — | — | — |
| 19 | C | C | B | C | A | C |
| 20 | C | C | C | B | A | C |
| 21 | C | C | C | B | B | C |
| 22 | C | C | B | C | A | B |
| 23 | C | C | B | C | A | C |
| 24 | C | C | C | C | A | A |
| 25 | C | C | C | B | A | A |
| 26 | B | B | C | B | A | A |
| 27 | B | B | C | C | A | A |
| 28 | C | C | C | C | A | A |
| 29 | C | B | C | C | A | A |
| 30 | C | C | C | C | C | A |
| 31 | C | C | C | C | C | A |
| 32 | — | — | — | — | — | — |
| 33 | — | — | — | — | — | — |
| 34 | — | — | — | — | B | A |
| 35 | — | — | — | — | B | A |
| 36 | A | B | C | C | A | A |
| 37 | A | C | C | C | A | A |
| 38 | — | — | C | C | B | A |
| 39 | C | C | C | C | C | A |
| 40 | — | — | — | — | — | — |
| 41 | — | — | — | — | — | — |
| 42 | A | A | C | B | A | A |
| 43 | C | C | C | C | A | A |
| 52 | A | B | C | B | A | A |
| 53 | A | B | C | C | A | A |
| 54 | C | C | B | C | A | A |
| 55 | C | C | C | C | A | A |
| 44 | A | B | C | B | A | A |
| 45 | B | C | C | C | A | A |
| 46 | A | A | C | B | A | A |
| 47 | C | C | C | C | A | A |
| 48 | — | — | — | — | — | — |
| 49 | — | — | — | — | — | — |
| 50 | B | B | C | B | A | A |
| 51 | B | C | B | C | A | A |
| 56 | — | — | — | — | — | — |
| 57 | — | — | — | — | — | — |
| 58 | C | C | C | C | A | A |
| 59 | C | C | C | C | A | A |
| 60 | A | C | B | B | A | A |
| 61 | C | C | C | C | A | A |
| 62 | C | C | C | C | A | A |
| 63 | C | C | A | C | A | A |
| 64 | — | — | — | — | — | — |
| 65 | — | — | — | — | — | — |
| 66 | — | — | — | — | — | — |
| 67 | C | C | C | B | B | A |
| 68 | C | C | C | A | C | B |
| 69 | — | — | — | — | — | — |
| 70 | — | — | — | — | B | A |
| 71 | — | — | — | — | B | A |
| 72 | — | — | — | — | B | A |
| 73 | C | C | A | C | C | C |
| 74 | C | C | A | B | C | C |

TABLE 3-continued

| Fungicidal effect of the compound of formula (I) | | | | | |
| --- | --- | --- | --- | --- | --- |
| 75 | C | C | A | B | C | C |

The more pertinent important features of the present invention have been outlined above in order that the detailed description of the invention which follows will be better understood and that the present contribution to the art can be fully appreciated. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

What is claimed is:

1. A benzothiazole derivative having the following general formula (I) or its (E) and (Z)-isomer,

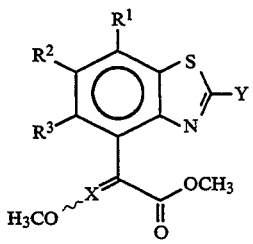

in which $R^1$, $R^2$ and $R^3$ independently of one another represent hydrogen halogen, straight and branched ($C_1$-$C_8$)alkyl, ($C_1$-$C_8$)halogenoalkyl or ($C_1$-$C_8$)alkoxy, X represents N or CH, Y represents a group -$OR^4$, -$SR^5$ or

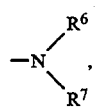

$R^4$, $R^5$, $R^6$ and $R^7$ independently of one another represent hydrogen, straight and branched ($C_1$-$C_{16}$)alkyl, ($C_3$-$C_8$)alkenyl, ($C_3$-$C_8$)alkynyl, ($C_3$-$C_8$)cycloalkyl, alkyl substituted with ($C_1$-$C_6$)alkoxy, or ($C_1$-$C_6$)halogenoalkyl, or represent a substituted phenyl, phenylacyl or benzyl group wherein the possible substituent on the phenyl, phenylacyl or benzyl group includes halogen, straight and branched ($C_1$-$C_8$)alkyl, ($C_1$-$C_8$)alkoxy, ($C_3$-$C_8$)alkenyl, ($C_3$-$C_8$)alkynyl, phenoxy, nitro, cyano and a five- or six-membered heterocyclic group containing one to four nitrogen atoms.

2. The compound according to claim 1, wherein $R^1$, $R^2 R^3$ independently of one another represent hydrogen, fluoro, chloro, methyl or ethyl, and $R^4$, $R^5$, $R^6$ and $R^7$ independently of one another represent hydrogen, straight and branched ($C_1$-$C_6$)alkyl, ($C_3$-$C_6$)alkenyl or ($C_3$-$C_6$)alkynyl.

3. The compound according to claim 1, wherein $R^4$, $R^5$, $R^6$ and $R^7$ independently of one another represents a phenyl group substituted with straight and branched ($C_1$-$C_6$)alkyl, ($C_3$-$C_6$)alkenyl, ($C_1$-$C_6$)alkoxy, ($C_3$-$C_6$)alkynyl, phenoxy, halogen, pyridinyl, pyrimidinyl, thiazolyl or imidazolyl on 2-, 3- or 4-position.

4. The compound according to claim 1, wherein the compound is (E,Z)-methyl 2-[2-(N,N'-dimethyl)amino-6-methyl-benzothiazol-4-yl]-2-methoxyiminoacetate, (E,Z)-methyl 2-[2-(N,N'-dimethyl)amino-6-methyl-benzothiazol-4-yl]-3-methoxypropenoate, (E,Z)-methyl 2-[2-(2-methyl)phenoxy-6-methylbenzothiazol-4-yl]-2-methoxyiminoacetate;

(E,Z)-methyl 2-[2-(3-methoxy)phenoxy-6-methylbenzothiazol-4-yl]-2-methoxyiminoacetate; or (E,Z)-methyl 2-(2-n-butylmercapto-6-methylbenzothiazol-4-yl)-2-methoxyiminoacetate 5. A method for combating phythopathogenic organisms and fungi present on an animal comprising applying to the animal an effective amount of a benzothiazole derivative having the following general formula (I) or its (E) and (Z)-isomer,

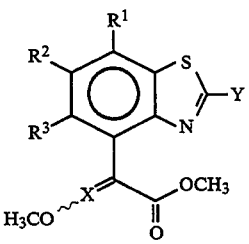

in which $R^1$, $R^2$ and $R^3$ independently of one another represent hydrogen, halogen, straight and branched ($C_1$-$C_8$)alkyl, ($C_1$-$C_8$)halogenoalkyl or ($C_1$-$C_8$)alkoxy, X represents N or CH, Y represents a group —$OR^4$, —$SR^5$ or

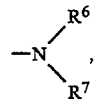

$R^4$, $R^5$, $R^6$ and $R^7$ independently of one another represent hydrogen, straight and branched ($C_1$-$C_{16}$)alkyl, ($C_3$-$C_8$)alkenyl, ($C_3$-$C_8$)alkynyl, ($C_3$-$C_8$ cycloalkyl, alkyl substituted with ($C_1$-$C_6$)alkoxy, or $C_1$-$C_6$)halogenoalkyl, or represent a substituted phenyl, phenylacyl or benzyl group wherein the possible substituent on the phenyl, phenylacyl or benzyl group includes halogen, straight and branched ($C_1$-$C_8$)alkyl, ($C_1$-$C_8$)alkoxy, ($C_3$-$C_8$)alkenyl, ($C_3$-$C_8$)alkynyl, phenoxy, nitro, cyano and a five- or six-membered heterocyclic group containing one to four nitrogen atoms.

* * * * *